United States Patent [19]

Doner et al.

[11] Patent Number: 4,961,868
[45] Date of Patent: Oct. 9, 1990

[54] GREASE COMPOSITION

[75] Inventors: John P. Doner, Sewell; Andrew G. Horodysky, Cherry Hill; John A. Keller, Jr., Pitman, all of N.J.

[73] Assignee: Mobil Oil Corporation, Fairfax, Va.

[21] Appl. No.: 319,841

[22] Filed: Mar. 7, 1989

Related U.S. Application Data

[60] Continuation of Ser. No. 210,136, Jun. 13, 1988, abandoned, which is a continuation of Ser. No. 81,590, Aug. 3, 1987, abandoned, which is a continuation of Ser. No. 851,637, Apr. 14, 1986, abandoned, and a continuation-in-part of Ser. No. 774,873, Sep. 12, 1985, abandoned, which is a continuation of Ser. No. 641,077, Aug. 15, 1984, abandoned, which is a continuation-in-part of Ser. No. 587,328, Mar. 7, 1984, abandoned, and a continuation-in-part of Ser. No. 641,078, Aug. 15, 1984, abandoned, which is a continuation-in-part of Ser. No. 577,454, Feb. 6, 1984, abandoned, and a continuation-in-part of Ser. No. 831,073, Feb. 18, 1986, abandoned, which is a continuation of Ser. No. 643,344, Aug. 22, 1984, abandoned, and a continuation-in-part of Ser. No. 643,346, Aug. 22, 1984, Pat. No. 4,600,517, and a continuation-in-part of Ser. No. 792,168, Oct. 25, 1985, abandoned, which is a continuation of Ser. No. 643,347, Aug. 22, 1984, abandoned, and a continuation-in-part of Ser. No. 769,827, Aug. 27, 1985, abandoned, and a continuation-in-part of Ser. No. 769,826, Aug. 27, 1985, Pat. No. 4,743,386, which is a continuation-in-part of Ser. No. 682,579, Dec. 17, 1984, abandoned, which is a continuation of Ser. No. 445,883, Dec. 1, 1982, abandoned, said Ser. No. 769,826, is a continuation-in-part of Ser. No. 638,609, Aug. 7, 1984, Pat. No. 4,571,248, which is a division of Ser. No. 456,880, Jan. 10, 1983, Pat. No. 4,486,321, and a continuation-in-part of Ser. No. 769,912, Aug. 27, 1985, abandoned, and a continuation-in-part of Ser. No. 769,837, Aug. 27, 1985, Pat. No. 4,655,948, and a continuation-in-part of Ser. No. 641,079, Aug. 15, 1984, Pat. No. 4,582,617, which is a continuation-in-part of Ser. No. 519,878, Aug. 3, 1983, abandoned.

[51] Int. Cl.$^5$ ............................................ C10M 117/04
[52] U.S. Cl. .................................. 252/32.7 E; 252/34; 252/41; 252/49.6
[58] Field of Search .................. 252/32.7 E, 34, 41, 252/49.6

[56] References Cited

U.S. PATENT DOCUMENTS

| | | | |
|---|---|---|---|
| 2,053,474 | 9/1936 | Graves et al. | 260/98 |
| 2,813,830 | 11/1957 | Trautman | 252/49.6 |
| 2,815,325 | 12/1957 | Pohorilla et al. | 252/42.1 |
| 2,943,054 | 6/1960 | Worth | 252/40.7 |
| 2,975,134 | 3/1961 | Cook | 252/40.7 |
| 3,009,791 | 11/1961 | Emrick | 44/63 |
| 3,125,523 | 3/1964 | Siegart et al. | 252/33.6 |
| 3,125,524 | 3/1964 | Siegart et al. | 252/33.6 |
| 3,125,525 | 3/1964 | Siegart et al. | 252/33.6 |
| 3,361,672 | 1/1968 | Andress et al. | 252/49.6 |
| 3,625,899 | 12/1971 | Sawyer | 252/75 |
| 3,697,574 | 10/1972 | Piasek | 260/462 R |
| 3,704,308 | 11/1972 | Piasek et al. | 260/462 R |
| 3,711,411 | 1/1973 | Sawyer et al. | 252/78 |
| 3,711,412 | 1/1973 | Sawyer et al. | 252/78 |
| 3,751,365 | 8/1973 | Piasek et al. | 252/49.6 |
| 3,758,407 | 9/1973 | Harting | 252/18 |
| 4,016,092 | 4/1977 | Andress | 252/32.5 |
| 4,140,492 | 2/1979 | Feldman et al. | 44/62 |
| 4,159,957 | 7/1979 | deVries | 252/33.4 |
| 4,370,248 | 1/1983 | Horodysky et al. | 252/49.6 |
| 4,374,032 | 2/1983 | Gemmill et al. | 252/49.6 |
| 4,376,712 | 3/1983 | Horodysky et al. | 252/49.6 |
| 4,382,006 | 5/1983 | Horodysky | 252/49.6 |
| 4,389,322 | 6/1983 | Horodysky | 252/49.6 |
| 4,406,802 | 9/1983 | Horodysky et al. | 252/49.6 |
| 4,410,438 | 10/1983 | Horodysky | 252/49.6 |
| 4,440,656 | 4/1984 | Horodysky | 252/49.6 |
| 4,472,289 | 9/1984 | Horodysky et al. | 252/49.6 |
| 4,486,321 | 12/1984 | Horodysky et al. | 252/46.3 |
| 4,524,005 | 6/1985 | Horodysky | 252/49.6 |
| 4,529,529 | 7/1985 | Horodysky | 252/49.6 |
| 4,582,617 | 4/1986 | Doner et al. | 252/32.7 |

FOREIGN PATENT DOCUMENTS

| | | |
|---|---|---|
| 0067002 | 12/1982 | European Pat. Off. . |
| 0075478 | 3/1983 | European Pat. Off. . |
| 0134063 | 3/1985 | European Pat. Off. . |
| 2103651 | 2/1983 | United Kingdom . |
| 2106133 | 4/1983 | United Kingdom . |
| 2107734 | 5/1983 | United Kingdom . |
| 2125431 | 3/1984 | United Kingdom . |

*Primary Examiner*—William R. Dixon, Jr.
*Assistant Examiner*—E. McAvoy
*Attorney, Agent, or Firm*—A. J. McKillop; C. J. Speciale; H. M. Flournoy

[57] ABSTRACT

The invention is a grease composition comprising a major proportion of a grease, a hydroxy-containing soap thickener and a minor amount of a compound prepared by reacting a boron compound with an organic compound containing oxygen, sulfur and/or nitrogen. Sulfur and/or phosphorous compounds are also incorporated into the composition.

36 Claims, No Drawings

GREASE COMPOSITION

CROSS REFERENCE TO RELATED APPLICATIONS

This is a continuation of copending application Ser. No. 210,136 filed on June 13, 1988, now abandoned, which is a continuation of copending application Ser. No. 081,590 filed on Aug. 3, 1987, now abandoned, which is a continuation of copending application Ser. No. 851,637 filed on Apr. 14, 1986, now abandoned which is a continuation-in-part of each of the following copending applications, each of which, as well as the application parent thereto, is incorporated herein by reference:

Application Ser. No. 774,873, filed Sept. 12, 1985, abandoned, which is a continuation of application Ser. No. 641,077, filed Aug. 15, 1984 abandoned, which is a continuation-in-part of U.S. application Ser. No. 587,328, filed Mar. 7, 1984, abandoned.

U.S. application Ser. No. 641,078, filed Aug. 15, 1984, abandoned which is a continuation-in-part of application Ser. No. 577,454, filed Feb. 6, 1984, abandoned.

U.S. application Ser. No. 831,073, filed Feb. 18, 1986, abandoned, which is a continuation of Ser. No. 643,344, abandoned, filed Aug. 22, 1984.

U.S. application Ser. No. 643,346, filed Aug. 22, 1984, now U.S. Pat. No. 4,600,517.

U.S. application Ser. No. 792,168, filed Oct. 25, 1985, abandoned, which is a continuation of application Ser. No. 643,347 filed Aug. 22, 1984 abandoned.

U.S. application Ser. No. 769,827, filed Aug. 27, 1985.

U.S. application Ser. No. 769,826, filed Aug. 27, 1985, U.S. Pat. No. 4,743,386 which is a continuation-in-part of application Ser. No. 682,579, filed Dec. 17, 1984, abandoned, which is a continuation of application Ser. No. 445,883, filed Dec. 1, 1982, abandoned U.S. Ser. No. 769,826 is a continuation-in-part of application Ser. No. 638,609, filed Aug. 7, 1984, U.S. Pat. No. 4,571,248 which is a division of application Ser. No. 456,880, filed Jan. 10, 1983, now U.S. Pat. No. 4,486,321.

U.S. application Ser. No. 769,912, filed Aug. 27, 1985, abandoned.

U.S. application Ser. No. 769,837, filed Aug. 27, 1985, U.S. Pat. No. 4,655,948.

U.S. application Ser. No. 641,079, filed Aug. 15, 1984, now U.S. Pat. No. 4,582,617, which is a continuation-in-part of U.S. application Ser. No. 519,878, filed Aug. 3, 1983, abandoned.

FIELD OF THE INVENTION

The invention is concerned with a novel group of grease compositions. It more particularly relates to a grease composition comprising oil, a thickener of which at least 10–15% of said thickener is a hydroxy-containing soap thickener and borated derivative of an organic compound containing optionally and preferably an oxygen, sulfur or nitrogen moiety which is reactive with a borating agent, and said borated derivation can optionally contain any other element of the Periodic Chart, the grease compositions optionally containing additional phosphorus and sulfur moieties.

DISCUSSION OF THE PRIOR ART

Borated alkoxylated alcohols have been used in commercial lubricant formulations to provide improvement in lubricity properties. This is known from U.S. Pat. No. 3,711,411, which discloses hydraulic fluids containing such products.

It is known further than borated esters and related borates can be used in other areas. For example, U.S. Pat. No. 3,740,358 teaches a phenol-aldehyde foamable composition containing a boron compound, e.g. a material formed by reacting boric acid or boric oxide with an aliphatic hydroxyl-containing compound.

U.S. Pat. No. 2,160,917 discloses lubricants containing low molecular weight borate esters, e.g., borate esters containing from 4 to 12 carbon atoms. The disclosed borates include the tributyl and trilauryl borates. Other patents include U.S. Pat. No. 3,014,870 (to mixtures of amine and certain boronic mono- or diesters); U.S. Pat. No. 3,108,966 (aryl boronic esters and thio acid ester lubricants); U.S. Pat. No. 3,133,951 (fuels containing dialkyl boron esters); U.S. Pat. No. 3,347,793 (teriaryalkyl boron esters) and U.S. Pat. No. 3,509,054 (esters or boron acids with 2,6-dialkyl-phenols).

From U.S. Pat. No. 4,328,113 it is also known that borated amines, such as borated hydrocarbyl mono-and diamines, are useful as friction reducers in lubricants, especially in lubricating oils.

Vicinal hydroxyl-containing alkyl carboxylates such as glycerol monooleate have found use as lubricity additives. U.S. Pat. No. 2,788,326 discloses some of the esters suitable for the present invention, e.g., glycerol monooleate, as minor components of lubricating oil compositions, U.S. Pat. No. 3,233,498 discloses, among others, the same ester as just mentioned, as an additive to other oils. U.S. Pat. No. 2,443,578 teaches esters wherein the free hydroxyl is found in the acid portion, as for example, in tartaric acid.

The above patents, as are numerous others, are directed to the use of such esters as additives. Other patents, such as U.S. Pat. Nos. 2,798,083; 2,820,014; 3,115,519; 3,282,917 and 3,309,318 as well as an article by R. R. Barnes et al. entitled "Synthetic Ester Lubricants" in Lubrication Engineering, August, 1975, pp. 454–457, teach lubricants prepared by polyhydric alcohols and acid containing no hydroxyl other than those associated with the acid function.

U.S. Pat. No. 4,374,032 corresponding to application Ser. No. 134,849, filed Mar. 28, 1980, discloses the use of borated adducts of oxazolines as a component of lubricating oils. U.S. Pat. No. 4,374,032 is incorporated herein by reference.

U.S. Pat. No. 4389,322 discloses the use of borated adducts of ethoxylated amides as a component of lubricating oils or greases. U.S. Pat. No. 4,389,322 is incorporated herein by reference.

The borated adducts of ethoxylated amides are prepared from ethoxylated compounds having the following generalized structure:

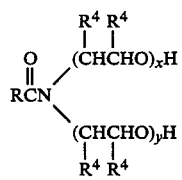

R is a hydrocarbyl group having from about 1 to about 60 (preferably 8 to 30) carbon atoms; R may be alkyl, alkenyl, aralkyl, alkylaryl, etc; x and y may be the same or different and are each a whole number from 0 to about 15, preferably 1 to 5, but the sum of x and y must equal 1 or more, or more preferably, 2 or more. $R^4$ is hydrogen or an alkyl or alkenyl radical of one to six carbon atoms and preferably is hydrogen or a methyl radical.

The borated derivatives can be prepared according to the discloses in U.S. Pat. No. 4,490,256 which is incorporated herein by reference or by treating the described amides with boric acid optionally in alcoholic solvents such as butanol or pentanol, or optionally hydrocarbon solvents such as benzene, toluene, xylene or mixtures thereof. Reaction temperatures of 70° to 260° C. can be used but 110° to 170° C. is preferred. Reaction times can be 1 to 10 hours or more. Up to a stoichiometric amount or an excess of boric acid can be used to produce a derivative containing 0.05% to 8% or more by weight of boron. Other methods are also available to make similar borated derivatives. For example, the ethoxylated amides may also be borated through transesterification with a trialkyl borate such as tributyl borate (often in the presence of boric acid).

The publication "Manufacture and Application of Lubricating Grease by C. J. Boner (Reinhold Publishing Company) 1954, pp. 155 and 436, 437 disclose the use of lithium soaps in grease making. The publication "Lubricant Additive" by C. V. Smalheer et al. (Leyuis-Hiles Co.) 1967, pp. 1–11, discloses the use of phosphonates and thiophosphonates as additives in lubricants. "Condensed Chemical Dictionary" 9th Edition, (Van Nostrand Reinhold Company) at pages 520 and 938 discloses the use of lithium hydroxystearate in grease making and zinc dialkyldithiophosphate as a lube oil additive.

These references, the publications by Boner and by Smalheer et al., and the "Condensed Chemical Dictionary" reference are incorporated herein by reference.

SUMMARY OF THE INVENTION

In accordance with the invention, there is provided an improved grease composition containing a major amount of a grease and a minor amount of the borated derivative of an organic compound containing optionally and preferably an oxygen, sulfur, or nitrogen moiety which is reactive with a borating agent which may be boric acid, boric oxide, metaborate or an alkyl borate of the formula $$(R^1O)_xB(OH)_y$$

wherein x is 1 to 3, y is 0 to 2, their sum being 3, and $R^1$ is an alkyl group containing from 1 to 6 carbon atoms or any other suitable boronating compound containing boron and a thickener containing at least about 15% by weight of a hydroxy-containing soap thickener. The above boron-containing organic compound can contain additionally any of the other elements of the Periodic Table. We believe, however, that the major benefits arise from the organic boron moieties such as those organic borates containing at least (a) carbon, hydrogen, oxygen, boron and other optional elements, (b) carbon, hydrogen, nitrogen, boron and other optional elements and combinations of (a) and (b) above. The presence of added phosphorus and sulfur compounds provides an even higher drop point.

Preferably the organic compound is overborated. By "overborated" is meant the presence in the borated product of more than a stoichiometric amount of boron.

DESCRIPTION OF SPECIFIC EMBODIMENTS

Examples of the types of sulfur, oxygen, and/or nitrogen containing borated organic compounds are:
alkoxylated alcohols
long-chain and short-chain alcohols
diols, preferably vicinal diols
mono- or polyamines
hydrocarbyl esters
oxazoline compounds
phenolic- and/or thio-amine Mannich bases
catechol, catechol-alcohol borates compounds, and catechol-amine borate compounds.

Each of the specific embodiments can additionally contain carboxylic acid or ester groups, amide groups, metallic salts groups and other groups without significantly detracting from the above disclosed invention.

Preparation of most of these borated compounds is disclosed in the copending application parent to this application, those applications having been incorporated herein by reference.

The Alkoxylated Alcohols

The borated alkoxylated alcohols are prepared by reacting an alkoxylated alcohol or mixtures of such alcohols having the formula $$RO(R^1O)_xH$$

wherein R is a hydrocarbyl group containing from 7 to 30 carbon atoms, preferably 9 to 18 carbon atoms, $R^1$ is a hydrocarbylene group containing from 2 to 4 carbon atoms and x is from 1 to 10, with a borating agent.

Long-Chain and Short-Chain Alcohols

In accordance with the invention, the long-chain and the borated short-chain alcohols are prepared by reacting an alcohol of the formula $$R^2OH$$

wherein $R^2$ is a $C_1$ to $C_{30}$ hydrocarbon group, or mixtures thereof, with the borating compound described below.

Preferably the alcohol is overborated. By "overborated" is meant the presence in the borated product of more than a stoichiometric amount of boron. Up to 100% to 1000% or more excess boron can be used.

The hydrocarbyl group includes straight and branched chain aliphatic groups, cycloaliphatic groups, aralkyl groups and alkaryl groups.

R may be a linear or branched alkyl group or mixtures thereof. It may also be cycloaliphatic group, an alkaryl group, an aryl alkyl group or a linear or branched group having at least one unsaturated bond, i.e., an alkenyl group, or mixtures thereof. Among the short-chain alcohols, the mixed $C_1$ to $C_{11}$ groups are preferred, with the more preferred being mixed $C_3$ to $C_{11}$ groups.

Short-chain alcohols that can be used for boration include:

| Chemical Name | Common Name | Formula |
|---|---|---|
| Methanol | Methyl alcohol | $CH_3OH$ |
| Ethanol | Ethyl alcohol | $CH_3CH_2OH$ |
| 1-Propanol | n-Propyl alcohol | $CH_3CH_2CH_2OH$ |
| 2-Propanol | Isopropyl alcohol | $(CH_3)_2CHOH$ |

-continued

| Chemical Name | Common Name | Formula |
|---|---|---|
| 1-Butanol | n-Butyl alcohol | $CH_3CH_2CH_2CH_2OH$ |
| 2-Methyl-1-propanol | Isobutyl alcohol | $(CH_3)_2CHCH_2OH$ |
| 2-Butanol | sec-Butyl alcohol | $CH_3CH_2CHOHCH_3$ |
| 2-Methyl-2-propanol | tert-Butyl alcohol | $(CH_3)_3COH$ |
| 1-Pentanol | n-Amyl alcohol | $CH_3(CH_2)_3CH_2OH$ |
| 2-Pentanol | sec-Amyl alcohol | $CH_3(CH_2)_2CHOHCH_3$ |
| 3-Pentanol | Diethylmethanol | $(CH_3CH_2)_2CHOH$ |
| 2-Methyl-1-butanol | Active amyl alcohol | $CH_3CH_2CH(CH_3)CH_2OH$ |
| 3-Methyl-1-butanol | Isoamyl alcohol | $(CH_3)_2CHCH_2CH_2OH$ |
| 2-Methyl-2-butanol | tert-Amyl alcohol | $CH_3CH_2COH(CH_3)_2$ |
| 2,2-Dimethyl-1-propanol | tert-Butyl methanol | $(CH_3)_3CCH_2OH$ |
| 3-Methyl-2-butanol | Methylisopropyl-methanol | $(CH_3)_2CHCHOHCH_3$ |
| 1-Hexanol | n-Hexyl alcohol | $C_6H_{13}OH$ |
| 4-Methyl-2-pentanol | Methylisobutyl-carbinol | $C_6H_{13}OH$ |
| 2-Methyl-1-pentanol | Methyl amyl carbinol | $C_6H_{13}OH$ |
| 2-Ethyl-1-butanol | Pseudohexyl alcohol | $C_6H_{13}OH$ |
| 1-Heptanol | n-Heptyl alcohol | $C_7H_{15}OH$ |
| 2-Heptanol (dl) | Methyl-n-amyl-carbinol | $C_7H_{15}OH$ |
| 1-Octanol | n-Octyl alcohol | $C_8H_{17}OH$ |
| 2-Octanol (dl) | Capryl alcohol | $C_8H_{17}OH$ |
| 2-Ethyl-1-hexanol | 2-ethyl-n-hexyl | $C_8H_{17}OH$ |
| Dimethyl-1-hexanol | iso-Octyl alcohol | $C_8H_{17}OH$ |
| 1-Nonanol | n-Nonyl alcohol | $C_9H_{19}OH$ |
| 2,6-Dimethyl-4-heptanol | Diisobutylcarbinol | $C_9H_{19}OH$ |
| 2-Propen-1-ol | allyl alcohol | $CH_2=CHCH_2OH$ |
| Ethenol | vinyl alcohol | $CH_2=CHOH$ |
| 2-Propyn-1-ol | propargyl alcohol | $CH=CCH_2OH$ |

The borated compounds of these short-chain alcohols is prepared in the manner described for preparing the long-chain borated alcohols in the incorporated applications and patents.

The Diols

The diols used in this invention preferably are vicinal, and of the formula $$R^3(OH)_2$$

where $R^3$ is a $C_8$ to $C_{30}$ hydrocarbyl group.

The Mono- or Polyamines

The borated amines useful in this invention are prepared by reacting an amine of the formula:

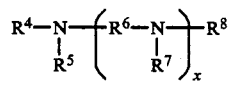

wherein x is 0 or 2, $R^4$, $R^5$, $R^7$ and $R^8$ are hydrogen or a $C_1$ to $C_{30}$ hydrocarbyl groups including alkyl groups containing 6 to 20 carbon atoms, hydroxyalkyl groups containing 2 to 4 carbon atoms, polyalkoxylated groups containing 6 to 20 carbon atoms and the corresponding members containing sulfur or additional oxygen, at least one of which is a hydrocarbyl group., i.e., is not hydrogen, and $R^6$ is a $C_2$ to $C_4$ alkylene group, with a borating compound.

The hydrocarbyl esters utilized herein have the formula $$R^9(COOR^{10})_n$$

wherein $R^9$ and $R^{10}$ are hydrocarbyl groups, or hydroxyhydrocarbyl groups, containing 1 to 40 carbon atoms, preferably 8 to 20 carbon atoms, at least one of $R^9$ or $R^{10}$ being a hydroxyhydrocarbyl group, and n is 1 to 5. The boron compound used for boronation is any of those noted previously.

The Borated Oxazoline Compounds

The oxazoline compounds used in this invention are believed to have the following generalized structure:

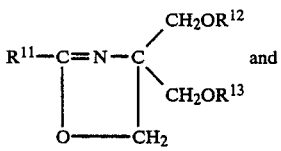

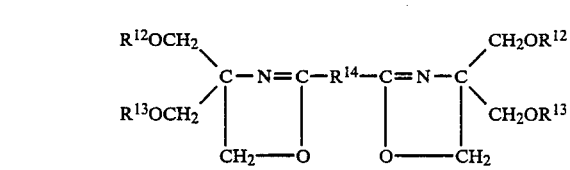

where $R^{11}$ and $R^{14}$ are hydrocarbyl or hydrocarbylene groups of one to fifty carbon atoms and optionally contain sulfur, oxygen, nitrogen, or halogen. Preferably $R^{11}$ and $R^{14}$ are of eight to twenty carbon atoms. $R^{12}$ and $R^{13}$ can be the same or different and can be hydrogen or have the generalized structure $$-\underset{\underset{O}{\|}}{C}-R^{15}$$

where $R^{15}$ is hydrogen or a hydrocarbyl group of one to fifty carbon atoms. Preferably, at least one of $R^{12}$ or $R^{13}$ is hydrogen available for boration.

More particularly, the product can be made by reacting molar amounts or more than molar amounts of a carboxylic acid of the formula $$R-COOH$$

with a hydroxyl amine such as tris(hydroxymethyl)aminomethane such that the oxazoline formed has the formula

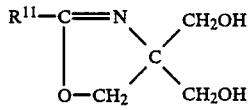

wherein $R^{11}$ is as defined above, followed by reacting the oxazoline with an appropriate borating agent.

The Borated Mercaptan Amine Aldehyde Products

The mercaptan amine aldehyde compounds that are borated for use in this invention are prepared as described in U.S. Pat. No. 4,486,321 and are mixtures of compounds, some of which have the following possible structures:

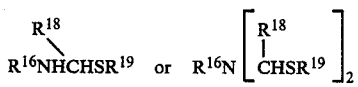

wherein $R^{16}$ is H or a $C_1$ to $C_{20}$ hydrocarbyl group, $R^{17}$ is a $C_2$ to $C_5$ alkylene group, $R^{18}$ is H or a $C_1$ to $C_8$ hydrocarbyl group (e.g., alkyl, alkenyl, cycloalkyl, alkaryl or aralkyl and $R^{19}$ is a $C_8$ to $C_{30}$ hydrocarbyl group, preferably an alkyl group. $R^{19}$ can be a straight chain or branched chain, with the straight chain being preferred.

The Borated Mannich Base (Phenol-Amine) Reaction Products

Borated Manich base reaction products are disclosed in pending U.S. application Ser. No. 682,579, filed Dec. 17, 1984, which is a continuation of Ser. No. 445,883, filed Dec. 1, 1982. This application (Ser. No. 682,579) is incorporated herein by reference.

The borated Mannich base reaction product described in application Ser. No. 628,579 is made by borating a product made by reacting an aldehyde, an amine and one or more phenols of the formula:

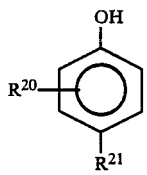

wherein $R^{20}$ is preferably hydrogen, but can be a $C_1$ to $C_{30}$ hydrocarbyl group, which may be an alkyl, alkenyl, aryl, alkaryl or aralkyl group. $R^{21}$ is a hydrocarbyl group, preferably alkyl or alkenyl containing 4 to 20 carbon atoms, and can additionally contain sulfur, oxygen and/or nitrogen atoms. $R^{21}$ can also be a polymeric group having a molecular weight up to between 1000 and 2000 and can be polypropyl, polybutenyl, polyisobutyl or the like.

Aldehydes that can be used are the aliphatic aldehydes, typified by formaldehyde or paraformaldehyde, acetaldehyde, and aldol (-hydroxy butyraldehyde); aromatic aldehydes, such as benzaldehyde and heterocyclic aldehydes, such as furfural. The aldehyde may contain a substituent group such as hydroxyl, halogen, nitro and the like. In short, any substituent can be used which does not take a major part in the reaction. Preference, however, is given to the aliphatic aldehydes, formaldehyde being particularly preferred.

The amines to be used include those which contain a primary amino group. Preferably, these include saturated and unsaturated aliphatic amines containing 1 to 20 carbon atoms. They more specifically include those of the structural formula:

$$R^{22}NH_2$$

wherein $R^{22}$ is a hydrocarbyl group having from 4 to 20 carbon atoms. These are preferably $C_6$ to $C_{18}$ straight or branched alkyl groups, but may be cyclic, the latter of which include cyclohexylamine. Straight chain amines are more preferred.

Other amines which can be used include:

(a) etheramines (hydrocarbyloxy hydrocarbyl amines) such as tri isodecyloxypropyl amine and etheramines of the formula $R^{22}OR^{23}NH_2$ where $R^{22}$ is as stated above and $R^{23}$ is a $C_1$ to $C_6$ hydrocarbyl group;

(b) N-hydrocarbyl hydrocarbylene diamines or triamines such as N-oleyl-1,3 propylene or N-coco-1,2-ethylenediamine or amines of the structure

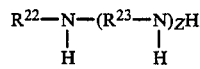

where $R^{22}$ and $R^{23}$ are as indicated above and Z is 1 to 3;

(c) etherdiamines (hydrocarbyloxy hydrocarbyl hydrocarbyl diamines) such as those of the structure

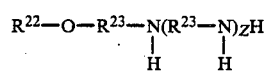

where $R^7$ and $R^9$ are as indicated above and Z is 1 to 3;

Also useful are aryl-hydrocarbylene amines and diamines.

Hydroxyl Containing Amides

The hydroxyl-containing amides useful in this invention have the formula

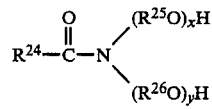

wherein $R^{24}$ is a hydrocarbyl group of 1 to 60 carbon atoms, preferably 2 to 50 carbon atoms, and most preferably 8 to 20 carbon atoms, including alkyl, alkenyl, alkoxyl, cycloalkenyl, cycloalkyl, alkaryl, aralkyl, etc. R can also contain oxygen, nitrogen or sulfur atoms.

$R^{25}$ and $R^{26}$ are each a hydrocarbylene group or a mixture of hydrocarbylene groups of 2 to 6 carbon atoms;

x is 0 to 15 and y is 0 to 15 provided that x+y equals at least 1. Preferably x+y equals 2 to 10 and more preferably 2 to 6. The terms "hydrocarbyl" and "hydroxyhydrocarbyl" include alkyl, aryl, aralkyl, alkaryl and cycloalkyl groups and can also include oxygen or sulfur.

The Catechol Borate, Catechol-Amine-Borate, and Catechol-Alcohol-Amine Borate Compounds The catechol borate and the borated catechol alcohol or borated catechol amine compounds are thought to have the following structure:

(1)

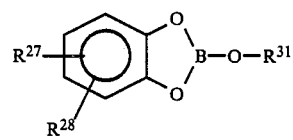

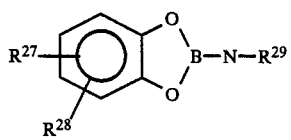

(2)

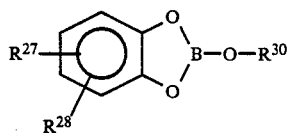

(3)

where $R^{27}$ and $R^{28}$ can each be hydrogen or $C_1$–$C_{40}$ hydrocarbyl. $R^{27}$ and $R^{28}$ optionally can also contain sulfur, oxygen, nitrogen or other such groups as long as the presence of these elements does not negatively affect performance of the additive compound.

$R^{29}$ can be $C_1$–$C_{40}$ hydrocarbyl and can contain, additionally, oxygen, sulfur and/or nitrogen-containing moieties.

$R^{30}$ can be $C_1$–$C_{40}$ hydrocarbyl and contain, additionally, oxygen, sulfur and/or nitrogen-containing moieties.

$R^{31}$ can be boron and/or catechol and/or ester and/or hydroxyl-containing moieties.

Thus the family of catechol borates useful in this invention can be represented by the following nonlimiting generic structure:

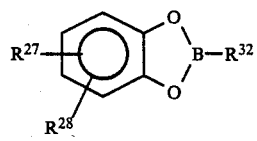

where $R^{32}$ can be $R^{29}$, $R^{30}$, or $R^{31}$, and can additionally contain oxygen, nitrogen, sulfur and boron as described above.

Organic Boron Compounds

Any substituent may be present in any of the above-mentioned organic borates provided that the substituent(s) do not negate the beneficial high-temperature dropping point improvement of the hydroxyl-containing soap thickened grease. These substituents contained in the organic borates can include any elements of the periodic chart of the Elements.

We believe that the carbon number ranges (and molecular weights) outlined above are not restricting, but can be extended for use in greases. For instance, we believe that borates of alcohol ethoxylates derived from hydrocarbyl groups containing only one or two carbon atoms would be as effective as the higher molecular weight species described herein. Thus short chain diols and mono- or polyamines, or oxazolines or Mannich base products derived from hydrocarbyl groups of 1–10 carbon atoms could be used in this invention.

Likewise, we believe that higher molecular weight borates, including borates of polymeric materials having molecular weights of up to 10,000 to 20,000 or more can be used in this invention. These organic borates can also contain 1, 2, 3, 4 ... 10 ... or even 100 or more borate linkages per organic borate molecule.

A narrow class of thickening agents is preferred to make the grease of this invention. Included among the preferred thickening agents are those containing at least a portion of alkali metal or alkaline earth metal soaps or amine soaps of hydroxyl-containing fatty acids, fatty glycerides and fatty esters preferably having from 12 to about 30 carbon atoms per molecule. The metals are typified by sodium, lithium, calcium and barium, with lithium being preferred. 12-hydroxystearic acid and glycerides and esters containing 12-hydroxystearates, 14-hydroxystearic acid, 16-hydroxystearic acid and 6-hydroxystearic acid are the preferred acids and fatty materials.

The entire amount of thickener need not be derived from the aforementioned preferred members. Significant benefit can be attained using as little as about 15% by weight of the hydroxystearate-containing thickener in the total thickener. A complementary amount, i.e., up to about 85% by weight of a wise variety of thickening agents can be used in the grease of this invention. Included among the other useful thickening agents are alkali and alkaline earth metal soaps of methyl-12-hydroxystearate, diesters of a $C_4$ to $C_{12}$ dicarboxylic acid and tall oily fatty acids. Other alkali or alkaline earth metal fatty acids containing from 12 to 30 carbon atoms and no free hydroxyl may be used. These include soaps of stearic and oleic acids. The aforementioned thickening agents can be produced in open kettles, pressurized vessels, or continuous manufacturing units. All of these production methods are commonly used for greases and have the necessary supporting equipment to process the grease during and after the manufacture of the thickener.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyamines, indanthrene, pigments such as perylimides, pyromellitdiimides, and ammeline, as well as certain hydrophobic clays. These thickening agents can be prepared from clays which are initially hydrophilic in character, but which have been converted into a hydrophobic condition by the introduction of long-chain hydrocarbon radicals into the surface of the clay particles prior to their use as a component of a grease composition, as, for example, be being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention.

The third member(s) that may be present in the grease composition are the phosphorus and sulfur moieties. Both of these can be present in the same molecule, such as in a metal or non-metal phosphorodithioate of the formula

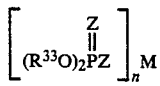

$$\left[ (R^{33}O)_2 P \overset{Z}{\underset{\|}{Z}} \right]_n M$$

wherein $R^{33}$ is a hydrocarbyl group containing 3 to 18 carbon atoms, or mixtures thereof, M is a metal or non-metal, n is the valence of M and Z is oxygen or sulfur, at least one being sulfur.

In this compound, $R^{33}$ is preferably an alkyl group and may be a propyl, butyl, pentyl, hexyl, octyl, decyl, dodecyl, tetradecyl or octadecyl group, including those derived from isopropanol, butanol, isobutanol, sec-butanol, 4-methyl-2-pentanol, 2-ethylhexanol, oleyl alcohol, and mixtures thereof. Further included are alkaryl groups such as butylphenyl, octylphenyl, nonylphenyl and dodecylphenyl groups.

The metals covered by M include those in Groups IA, IB, IIA, IIB, VIB and VIII of the Periodic Table. Some that may be mentioned are lithium, sodium, calcium, zinc, cadmium, silver, molybdenum and gold. Non-metallic ions include organic groups derived from vinyl esters each as vinyl acetate, vinyl ethers such as butyl vinyl ether and epoxides such as propylene oxide and 1,2-epoxydodecane, as well as organic amines such as $C_{10}$ to $C_{20}$ hydrocarbyl amines including oleylamine and N-oleyl-1,3-propylenediamine, diamines, imidazolines and oxazolines.

The intermediate phosphorodithioic acid may be also reacted with an epoxide such as propylene oxide followed by reaction with $P_2O_5$ to form acid phosphates which can optionally be further reacted with amines to form useful phosphorus and sulfur compounds. Phosphorodithionyl sulfides and disulfides can also be used. We believe that any alternate organic compounds containing phosphorus and sulfur would be effective in this invention.

The phosphorus and sulfur can also be supplied from the combination of two separate compounds, such as the combination of (1) a dihydrocarbyl phosphite having 2 to 10 carbon atoms in each hydrocarbyl group or mixtures of phosphites and (2) a sulfide such as sulfurized isobutylene, dibenzyl disulfide, sulfurized terpenes and sulfurized jojoba oil. The phosphites embrace the dibutyl, dihexyl, dioctyl, didecyl and similar phosphites. Phosphate esters containing 4 to 20 carbon atoms in each hydrocarbyl group, such as tributryl phosphate, tridecyl phosphate, tricresyl phosphate and mixtures of such phosphates, can also be used.

In summary, it is essentially to the practice of this invention, in which greases having vastly improved dropping points are obtained, that at least the first two of the above-mentioned ingredients be formulated into the composition. Thus:

First, with respect to the preparation of the grease, the total thickener will have at least about 15% by weight of a metal or non-metal hydroxy-containing soap therein, and there will be present from about 3% to about 20% by weight of total thickener based on the grease composition; and second, there will be added to the composition from about 0.01% to about 10% by weight thereof, preferably about 0.1% to about 2%, of a borated organic compound preferably containing oxygen, sulfur and/or nitrogen atoms, in which the borated organic compound preferably has been reacted in preferably at least an equimolar amount and, more preferably, an excess of a boron compound; and as a third component, the composition may have therein from 0.01% to about 10% by weight preferably, from 0.2% to 2% by weight of phosphorus- and sulfur-containing compounds or a mixture of two or more compounds which separately supply the phosphorus and sulfur moieties. If separate compounds are used, an amount of the mixture equivalent to the above concentration levels is used to supply desired amounts of phosphorus and sulfur.

It has been noted that, when the hydroxy-containing thickener is used with the borated organic compound or mixtures thereof, the drooping point of the grease is consistently unexpectedly higher than with a grease from the same grease vehicle and the same borated organic compound, but with a different thickener, e.g., a non-hydroxy-containing thickener. This absence of dropping point elevation is demonstrated in Examples 8, 16, 22, 28, 39, 47, 54, 61, 68 and 77. Thus, the broad invention is to a grease composition comprising the two components mentioned.

In general, the reaction products of the present invention may be employed in any amount which is effective for imparting the desired degree of friction reduction, antiwear activity, antioxidant activity, high temperature stability or antirust activity. In many applications, however, the borated organic compound and the phosphorus- and/or sulfur -containing compound(s) are effectively employed in combined amounts from about 0.02% to about 20% by weight, and preferably from about 0.2% to about 4% of the total weight of the composition.

The greases of the present invention can be made from either a mineral oil or a synthetic oil, or mixtures thereof. In general, mineral oils, both paraffinic, naphthenic and mixtures thereof, may be of any suitable lubricating viscosity range, as for example, from about 45 SSU at 100° F. to about 6000 SSU at 100° F., and preferably from about 50 to about 250 SSU at 210° F. These oils may have viscosity indexes ranging to about 100 or higher. Viscosity indexes from about 70 to about 95 are preferred. The average molecular weights of these oils may range from about 250 to about 800. In making the grease, the lubricating oil from which it is prepared is generally employed in an amount sufficient to balance the total grease composition, after accounting for the desired quantity of the thickening agent, and other additive components to be included in the grease formulation.

In instances where synthetic oils are desired, in preference to mineral oils, various compounds of this type may be successfully utilized. Typical synthetic vehicles include polyisobutylene, polybutenes ,hydrogenated polydecenes, polypropylene glycol, polyethylene glycol, trimethylol propane esters, neopentyl and pentaerythritol esters, di(2-ethylhexyl) sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

The metallic soap grease compositions containing one or more of the borated organic compounds, and, optionally, one or more of the sulfur and phosphorus combinations described herein provide advantages in increased dropping point, improved grease consistency properties, antirust characteristics and potential antifatigue, antiwear and antioxidant benefits unavailable in any of the prior greases known to us. The grease of this invention is unique in that it can be preferably manufactured by the admixture of additive quantities of the organic borates or oil concentrates or dispersions of such organic borates to the fully formed soap grease after completion of saponification.

Alcohol Boron Compounds

EXAMPLE 1

Preparation of Tri(4-methyl-2-pentyl) Borate

Approximately 306 grams of 4-methyl-2-pentanol, 100 grams of toluene, and 62 grams of boric acid were charged to a 2-liter glass reactor having an inert nitrogen atmosphere and equipped with heater, agitator, and Dean-Stark tube with condenser. The reactants were heated up to about 155° C. for a period of about 5 hours with agitation until water evolution during azeotropic distillation ceased. Approximately 52 grams of water was collected. The product was vacuum topped at about 155° C. to remove volatile solvent and filtered hot through diatomaceous earth to form a clear, waterwhite liquid.

Tributyl Borate

A commercial grade of tributyl borate was also used in the tests reported. It could have been made in the laboratory by the reaction of n-butanol with boric acid, optionally in the presence of a solvent such as benzene.

EXAMPLE 2

A lithium hydroxystearate grease thickener was prepared by saponification of a mixture containing 12-hydroxystearic acid (50%) and the tri-glyceride thereof (50%) with lithium hydroxide in a mineral oil vehicle (ISO 150 viscosity grade of a 70/30 mixture of naphthenic and paraffinic stocks) at about 350° F. in a closed contactor. After depressuring and dehydration of the thickener in an open kettle sufficient mineral oil was added to reduce the thickener content to about 9.0%. After cooling to 210° F., a typical grease additive package, consisting of an amine antioxidant, phenolic antioxidant, metallic dithiophosphate, sulfur-containing metal deactivator an nitrogen containing antirust additives, was added. The dropping point of this base grease was 395° F.

EXAMPLE 3

Two weight percent of the borated (4-methyl-2-pentyl)alcohol of Example 1 where added to the base grease of Example 2 at about 110° to about 115° C.

EXAMPLE 4

Two weight percent of the tributyl borate described above were added to the base grease of Example 2 at about 110° C. to 115° C.

EXAMPLE 5

A lithium hydroxystearate grease thickener was prepared by saponification of a mixture containing 12-hydroxystearic acid (50%) and the tri-glyceride thereof (25%) and 25% of $C_{22}$ fatty acids containing no OH groups with lithium hydroxide in a mineral oil vehicle (ISO 150 viscosity grade of a 70/30 mixture of naphthenic and paraffinic stocks) at about 350° F. in a closed contactor. After depressuring and dehydration of the thickener in an open kettle sufficient mineral oil was added to reduce the thickener content to about 8%. The dropping point of this grease was 407° F. (208° C.). This grease contained no phosphorus or sulfur additives.

EXAMPLE 6

Two weight percent of the tributylborate described above was added to the base grease of Example 5 at about 110° C. to 115° C.

EXAMPLE 7

A lithium stearate grease thickener was prepared by saponification of stearic acid with lithium hydroxide in a mineral oil vehicle (ISO 150 viscosity grade of a 70/30 mixture of naphthenic and paraffinic stocks) at about 350° F. in a closed contactor. After depressuring an dehydration of the thickener in an open kettle sufficient mineral oil was added to reduce the thickener content to about 10.0%. The grease thickener of this example contained no hydroxyl groups in the lithium stearate soap. The dropping point of this grease was 403° F. (206° C.).

EXAMPLE 8

Two weight percent of the tributyl borate described above and two wt. percent zinc dialkyl dithiophosphates (derived from mixed $C_3$ secondary (isopropyl) and $C_6$ primary alcohols) was added to the base grease of Example 7 at about 110° C. to 115° C.

ASTM D2265 Dropping Point Test results for the various greases are shown in Table V.

TABLE I

| Sample | D2265 Dropping Point °C. |
| --- | --- |
| Base grease of Example 2 (containing amine antioxidant, phenolic antioxidant, 1.5% zinc dithiophosphate and sulfur-containing metal deactivator and nitrogen containing antirust additives | 202° C. |
| Grease of Example 3 | 323° C. |
| Grease of Example 4 | 317° C. |
| Grease of Example 5 | 208° C. |
| Grease of Example 6 | 253° C. |
| Grease of Example 7 | 206° C. |
| Grease of Example 8 | 204° C |

As can be seen from above (Ex. 7 and 8), no dropping point improvement is derived unless a portion of the thickener contains a hydroxyl group in the soap. As can also be seen above, the phosphorus and/or sulfur sources are not required, but can often enhance the dropping point improving properties of these borates when admixed with a grease manufacture with a hydroxyl-containing thickener.

The above mentioned zinc dithiophosphate was derived from mixed $C_3$ secondary (isopropyl) and $C_6$ primary alcohols.

In order to more clearly set forth applicants' invention the data disclosed in the copending parent application has been abstracted into the body of data as shown in Table II. From this table it is readily discernible that the combination of a borated organic compound and a hydroxy bearing thickener results in a grease having a substantially increased dropping point temperature. The addition of even more sulfur and phosphorus compounds such as zinc thiophosphate further enhances the dropping point.

TABLE II

| Item Number | Borated Compound | % Amount of Borated Compound | % of Hydroxy Thickener | Percent of Added Zinc Thiophosphorate | Dropping Point ° C. |
|---|---|---|---|---|---|
| 3 | Alcohol Ethoxylate | 0 | 9.0 | 1.5 | 202 |
| 4 | " | 2 | 9.0 | 1.5 | 237 |
| 5 | " | 2 | 9.0 | 1.5 | 305 |
| 6 | " | 0 | 0 | 0 | 209 |
| 7 | " | 0 | 4.5 | 0.75 | 190 |
| 8 | " | 2 | 0 | 0 | 207 |
| 10 | Alcohols | 0 | 9 | 1.5 | 202 |
| 11 | " | 2 | 9 | 1.5 | 323 |
| 12 | " | 2 | 9 | 1.5 | 317 |
| 13 | " | 0 | 8 | 0 | 208 |
| 14 | " | 2 | 8 | 0 | 253 |
| 15 | " | 0 | 0 | 0 | 206 |
| 16 | " | 2 | 0 | 2 | 204 |
| 18 | " | 0 | 9 | 1.5 | 201 |
| 19 | " | 2 | 9 | 1.5 | 327 |
| 20 | " | 0 | 0 | 0 | 209 |
| 21 | " | 0 | ~4½ appx. | 0.75 | 190 |
| 22 | " | 2 | 0 | 0 | 207 |
| 24 | Organic Diols | 0 | 9 | 1.5 | 201 |
| 25 | " | 2 | 9 | 1.5 | 305 |
| 26 | " | 0 | 0 | 0 | 209 |
| 27 | " | 0 | 4.5 | 0 | 190 |
| 28 | " | 2 | 0 | 0 | 207 |
| 31 | Organic Diamines | 0 | 8 | 0 | 199 |
| 32 | " | 0 | 9 | 1.5 | 200 |
| 33 | " | 0.5 | 9 | 1.5 | 310 |
| 34 | " | 1.0 | 9 | 1.5 | 300 |
| 35 | " | 0.5 | 8 | 0 | 236 |
| 36 | " | 2 | 8 | 0 | 258 |
| 37 | " | 0 | 0 | | 209 |
| 38 | " | 0 | 4.5 | | 190 |
| 39 | " | 2 | 0 | | 207 |
| 42 | Hydroxyl-Containing Ester | 0 | 9 | 1.5 | 202 |
| 43 | " | 2 | 9 | 1.5 | 240 |
| 44 | " | 2 | 9 | 1.5 | 290 |
| 45 | " | 0 | 0 | 0 | 209 |
| 46 | " | 0 | 4.5 | .75 | 190 |
| 47 | " | 2 | 0 | 0 | 207 |
| 48 | Oxazoline Compounds | 0 | 9 | 1.5 | 202 |
| 49 | " | 0 | 10 | 0 | 202 |
| 50 | " | 0 | 0 | 0 | 207 |
| 51 | " | 2 | 10 | 0 | 232 |
| 52 | " | 2 | 10 | 0 | 267 |
| 53 | " | 2 | 10 | 1.5 | 319 |
| 54 | " | 2 | 0 | 0 | 201 |
| 55 | Phenolic Amine Compounds | 0 | 9 | 1.5 | 202 |
| 56 | " | 0 | 10 | 0 | 202 |
| 57 | " | 0 | 0 | 0 | 207 |
| 59 | " | 2 | 10 | 0 | 264 |
| 60 | " | 2 | 10 | 1.5 | 299 |
| 61 | " | 2 | 0 | 0 | 203 |
| 62 | Hydroxyl-Containing Amides | 0 | 9 | 1.5 | 202 |
| 63 | " | 0 | 10 | 0 | 202 |
| 65 | " | 2 | 10 | 0 | 253 |
| 66 | " | 2 | 10 | 1.5 | 307 |
| 67 | " | 0 | 0 | 0 | 207 |
| 68 | " | 2 | 0 | 0 | 201 |
| 69 | Catechol Compounds | 0 | 9 | 1.5 | 202 |
| 70 | " | 0 | 10 | 0 | 202 |
| 71 | " | 0 | 0 | 0 | 207 |
| 72 | " | 2 | 10 | 0 | 243 |
| 73 | " | 2 | 10 | 0 | 254 |
| 74 | " | 2 | 9 | 1.5 | 302 |
| 75 | " | 2 | 10 | 0 | 302 |
| 76 | " | 2 | 9 | 1.5 | 309 |
| 77 | " | 2 | 0 | 0 | 199 |

*Examples 10-16 are examples 2-8 described in this specification.

We claim:

1. An improved grease composition comprising a major proportion of a lubricating compound and:
   (a) a borated derivative of an organic compound,
   (b) a metal or amine derivative of a hydroxy-containing or polyhydroxy-containing carboxylate soap thickener wherein said metal is selected from calcium and lithium, and
   (c) a phosphorus and sulfur containing compound selected from the group consisting of zinc dihydrocarbyldithiophosphates; said borated organic compound, said hydroxy-containing thickener and said phosphorus and sulfur containing compound each being present in an amount sufficient to increase the dropping point over the dropping point of a grease without said borated organic compound and said phosphorus sulfur containing compound.

2. The composition of claim 1 wherein hydrocarbyl is selected from alkyl and alkaryl groups having from about 3 to about 18 carbon atoms.

3. The composition of claim 2 wherein the hydrocarbyl group in an alkyl group.

4. The composition of claim 3 wherein the alkyl group is derived from mixed $C_3$ secondary and $C_6$ primary alcohols.

5. An improved grease composition comprising a major proportion of a lubricating component and:
   (a) means for elevating the dropping point of a grease comprising a sufficient amount of a borated derivative of an organic compound; and
   (b) a metal or amine derivative of a hydroxy-containing or polyhydroxy-containing carboxylate soap thickener wherein said metal is selected from lithium and calcium, and
   (c) a phosphorus and sulfur containing compound selected from the group consisting of zinc dihydrocarbyldithiophosphates.

6. The composition of claim 5 wherein said borated derivative is present in said grease composition in an amount of between about 0.2 and about 10 percent by weight.

7. The composition of claim 5 wherein the total amount of thickener added is between about 3 and about 20 percent by weight of the total composition.

8. The composition of claim 7 wherein the thickener contains at least 15 percent by weight of hydroxy-containing thickener.

9. The composition of claim 5 wherein said grease contains between about 0.2 and about 10 percent by weight of said phosphorus- and sulfur- containing compounds.

10. The composition of claim 5 wherein said hydroxy-containing soap thickener is lithium hydroxystearate.

11. The composition of claim 5 wherein the borated derivative is the reaction product made by reacting an alkoxylated alcohol of the formula $$(RO)(R^1O)_xH$$

wherein R is a hydrocarbyl group or a mixture of hydrocarbyl groups, containing from 1 to 50 carbon atoms, $R^1$ is a $C_2$ to $C_4$ hydrocarbylene group and x is from 1 to 7 with a boron compound.

12. The composition of claim 5 wherein the borated derivative is the reaction product made by reacting an alcohol of the formula $$R^2OH$$

wherein $R^2$ is a hydrocarbyl group, or mixture thereof, containing from 1 to 30 carbon atoms, with a boron compound.

13. The composition of claim 5 wherein the borated derivative is the reaction product made by reacting a diol of the formula $$R^3(OH)_2$$

wherein $R^3$ is a hydrocarbyl group containing from 2 to 30 carbon atoms with a boron compound.

14. The composition of claim 5 wherein the borated derivative is the reaction product made by reacting an amine of the formula

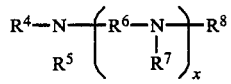

wherein x is 0 to 2, $R^4$, $R^5$, $R^7$ and $R^8$ are hydrogen or hydrocarbyl groups containing from 1 to 30 carbon atoms, hydroxyalkyl groups containing 2 to 4 carbon atoms, a polyalkoxylated group containing 6 to 20 carbon atoms or th latter group containing sulfur or additional oxygen, at least one of $R^4$, $R^5$, $R^7$ and $R^8$ being a non-hydrogen group and $R^6$ is a $C_2$ to $C_4$ alkylene group, with a boron compound.

15. The composition of claim 5 wherein the borated derivative is the reaction product made by reacting an ester of the formula $$R^9(COOR^{10})_n$$

wherein n is 1 to 5 and $R^9$ and $R^{10}$ are hydrocarbyl or hydroxyhydrocarbyl groups containing 1 to 20 carbon atoms, at least one of $R^9$ and $R^{10}$ being a hydroxyhydrocarbyl group with a boron compound.

16. The composition of claim 5 wherein the borated derivative is the reaction product made by reacting an oxazoline of the generalized structure

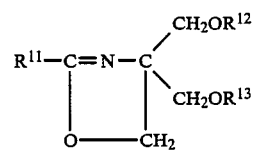

where $R^{11}$ is a hydrocarbyl or hydrocarbylene group of one to fifty carbon atoms, at least one of $R^{12}$ or $R^{13}$ is hydrogen and the other is hydrogen or has the generalized structure

where $R^{14}$ is hydrogen or a hydrocarbyl group of one to fifty carbon atoms with a boron compound.

17. The composition of claim 5 wherein the borated derivative is the reaction product made by reacting an oxazoline of the generalized structure

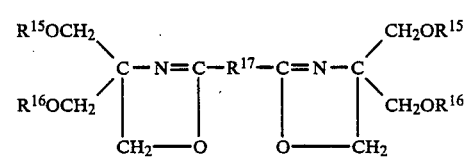

where $R^{17}$ is a hydrocarbyl or hydrocarbylene group of one to fifty carbon atoms, at least one of $R^{15}$ or $R^{16}$ is hydrogen and the other is hydrogen or has the generalized structure

where $R^{18}$ is hydrogen or a hydrocarbyl group of one to fifty carbon atoms with a boron compound.

18. The composition of claim 5 wherein the borated derivative is the reaction product made by reacting an amine with an aldehyde and a phenol or mercaptan and subsequently reacting the resulting product with a boron compound, the hydroxy-containing thickener and borated amine condensation product being present in sufficient quantities to effect an increase in the dropping point of said grease.

19. The composition of claim 5 wherein the borated derivative is the reaction product made by reacting an hydroxyl-containing amide having the structural formula:

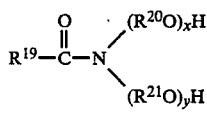

wherein
$R^{19}$ is a hydrocarbyl group of 1 to 60 carbon atoms and can additionally contain sulfur, oxygen and/or nitrogen;
$R^{20}$ and $R^{21}$ are each a hydrocarbylene group or a mixture of hydrocarbylene groups of 2 to 6 carbon atoms;
x is 0 to 15, and
y is 0 to 15, provided that x+y equals at least 1 with a boron compound.

20. The composition of claim 5 wherein the lubricating component is selected from the group consisting of mineral oils, synthetic oils, or mixtures thereof.

21. The composition of claim 20 wherein the synthetic oils are polglycols, synthetic hydrocarbons, alkyl benzenes, dibasic acid esters, polyol esters, phosphate esters or mixtures thereof.

22. The composition of claim 5 wherein the borated derivative additionally contains oxygen, sulfur, and/or nitrogen which is reactive with a borating agent.

23. The composition of claim 5 wherein the borated derivative of an organic compound contains additionally any of the elements of the Periodic Table of the Elements.

24. The composition of claim 5 wherein the borated derivative is a polymeric organic borate.

25. A method for elevating the dropping point of a grease composition comprising incorporating into said grease product means for elevating the dropping point of said grease comprising an organic boron compound, a metal or amine derivative of a hydroxy-containing or polyhydroxy-containing soap carboxylate thickener wherein said metal is selected from lithium and calcium and a phosphorus and sulfur containing compound selected from the group consisting of zinc dihydrocarbyldithiophosphates.

26. The method of claim 25 wherein the hydroxy-containing soap thickener is at least 15% by weight of the total thickener is said grease composition.

27. The method of claim 25 wherein the borated derivative additionally contains oxygen, sulfur and/or nitrogen which is reactive with a borating agent.

28. The method of claim 25 wherein the borated derivative contains additionally any of the elements of the Periodic Table of the Elements.

29. The method of claim 25 wherein the borated organic compound is a polymeric organic borate.

30. A method for making grease wherein a liquid lubricant is mixed with a thickening agent, the improvement comprising adding to said grease means for elevating the dropping point of a grease comprising a borated organic compound, a metal or amine derivative of a hydroxy-containing or polyhydroxy-containing soap carboxylate thickener wherein said metal is selected from lithium and calcium and a phosphorus and sulfur containing compound selected from the group consisting of zinc dihydrocarbyldithiophosphates.

31. The method of claim 30 wherein the borated derivative additionally contains oxygen sulfur and/or nitrogen which is reactive with a borating agent.

32. The method of claim 30 wherein the borated derivative contains additionally any of the Periodic Table of the Elements.

33. The method of claim 30 wherein the borated organic compound is a polymeric organic borate.

34. An improved grease composition comprising a major proportion of a lubricating component and: comprising
(a) a borated derivative of an organic compound containing an hydroxyl, epoxide, thiol or nitrogen moiety which is reactive with a borating agent, and
(b) a metal or amine derivative of a hydroxy-containing or polyhydroxy-containing carboxylate soap thickener wherein said metal is selected from lithium and calcium, and
(c) a phosphorus and sulfur containing compound selected from the group consisting of zinc dihydrocarbyldithiophosphates.

35. A method for elevating the dropping point of a grease composition comprising incorporating into said grease means for elevating the dropping point thereof; comprising an amount sufficient to significantly improve the dropping point of
(a) a borated derivative of an organic compound containing an hydroxyl, epoxide, thiol or nitrogen moiety,
(b) a metal or amine derivative of a hydroxy-containing or polyhydroxy-containing carboxylate soap thickener wherein said metal is selected from lithium and calcium, and
(c) a phosphorus and sulfur containing compound selected from the group consisting of zinc dihydrocarbyldithiophosphates.

36. An improved grease composition comprising proportion of a component and:
(a) means for elevating the dropping point of a grease comprising an amount sufficient to significantly improve the dropping point of a borated derivative of an organic compound containing an hydroxyl, epoxide, thiol or nitrogen moiety which is reactive with a borating agent,
(b) a metal or amine derivative of a hydroxy-containing or polyhydroxy-containing carboxylate soap thickener wherein said metal is selected from lithium and calcium, and
(c) a phosphorus and sulfur containing compound selected from the group consisting of zinc dihydrocarbyldithiophosphates.

* * * * *

UNITED STATES PATENT AND TRADEMARK OFFICE
CERTIFICATE OF CORRECTION

PATENT NO. : 4,961,868

DATED : October 9, 1990

INVENTOR(S) : John P. Doner et al

It is certified that error appears in the above-identified patent and that said Letters Patent is hereby corrected as shown below:

In column 20, line 54, "comprising proportion of a component and:" should be --comprising proportion of a lubricating component and:--.

Signed and Sealed this

Sixth Day of October, 1992

Attest:

DOUGLAS B. COMER

Attesting Officer

Acting Commissioner of Patents and Trademarks